US012599733B2

(12) United States Patent
Hull et al.

(10) Patent No.: US 12,599,733 B2
(45) Date of Patent: Apr. 14, 2026

(54) WEANING METHOD AND RELATED PRODUCTS

(71) Applicant: Telesair, Inc., Irvine, CA (US)

(72) Inventors: Andrew Hull, Laguna Niguel, CA (US); Qing Wang, Palo Alto, CA (US); Yong Liu, Orange, CA (US)

(73) Assignee: Telesair, Inc., Irvine, CA (US)

( * ) Notice: Subject to any disclaimer, the term of this patent is extended or adjusted under 35 U.S.C. 154(b) by 25 days.

(21) Appl. No.: 18/076,610

(22) Filed: Dec. 7, 2022

(65) Prior Publication Data

US 2024/0189529 A1      Jun. 13, 2024

(51) Int. Cl.
*A61M 16/00*          (2006.01)

(52) U.S. Cl.
CPC ... *A61M 16/024* (2017.08); *A61M 2202/0208* (2013.01); *A61M 2205/3303* (2013.01); *A61M 2205/3334* (2013.01); *A61M 2205/52* (2013.01)

(58) Field of Classification Search
CPC ................................................... A61B 5/4836
See application file for complete search history.

(56)              References Cited

U.S. PATENT DOCUMENTS

| | | |
|---|---|---|
| 4,121,583 A | 10/1978 | Chen |
| 4,809,706 A | 3/1989 | Watson et al. |
| 5,207,623 A | 5/1993 | Tkatchouk et al. |
| 5,571,075 A | 11/1996 | Bullard |

| | | | |
|---|---|---|---|
| 5,984,873 A | 11/1999 | Crumb et al. | |
| 6,131,569 A | 10/2000 | Schuster | |
| 2002/0035927 A1 | 3/2002 | Kutt et al. | |
| 2004/0006926 A1 | 1/2004 | Neeley et al. | |
| 2005/0059530 A1 | 3/2005 | Chang | |
| 2007/0023041 A1 | 2/2007 | Wang | |
| 2008/0132383 A1 | 6/2008 | Einav et al. | |
| 2008/0236582 A1* | 10/2008 | Tehrani ............... | A61M 16/024 |
| | | | 128/204.22 |
| 2008/0295839 A1* | 12/2008 | Habashi ............ | A61M 16/0051 |
| | | | 128/204.22 |
| 2011/0067697 A1* | 3/2011 | Lellouche ............ | A61M 16/10 |
| | | | 128/204.23 |

(Continued)

FOREIGN PATENT DOCUMENTS

| | | |
|---|---|---|
| CN | 204910621 U | 12/2015 |
| CN | 110051989 A | 7/2019 |

(Continued)

OTHER PUBLICATIONS

Office Action issued on May 10, 2023, in related U.S. Appl. No. 18/076,577, 18 pages.

(Continued)

*Primary Examiner* — Joseph D. Boecker
*Assistant Examiner* — Brian T Khong
(74) *Attorney, Agent, or Firm* — Maier & Maier, PLLC

(57)              ABSTRACT

A method for assisting a patient in weaning from a therapy, the method being executed by a controller, and the controller being configurable with different at least one weaning strategy. The method includes setting, based on at least one input by a user, a target weaning strategy among the at least one weaning strategy, where the at least one input corresponds to a clinical decision determined by the user.

14 Claims, 5 Drawing Sheets

(56) References Cited

U.S. PATENT DOCUMENTS

| | | | |
|---|---|---|---|
| 2011/0120470 A1* | 5/2011 | Bowerbank | G06Q 10/06 |
| | | | 128/204.23 |
| 2011/0146687 A1 | 6/2011 | Fukushima | |
| 2012/0116179 A1 | 5/2012 | Drew et al. | |
| 2012/0315614 A1 | 12/2012 | Krauza | |
| 2013/0160767 A1 | 6/2013 | Abella | |
| 2014/0000609 A1* | 1/2014 | Steinhauer | A61M 16/0057 |
| | | | 128/204.23 |
| 2014/0107500 A1 | 4/2014 | Stamatopoulos et al. | |
| 2014/0235959 A1* | 8/2014 | Jafari | A61M 16/024 |
| | | | 600/533 |
| 2015/0224270 A1 | 8/2015 | Frandson | |
| 2015/0231443 A1 | 8/2015 | Halliday | |
| 2015/0231447 A1 | 8/2015 | Hsu | |
| 2015/0258560 A1 | 9/2015 | Ashby et al. | |
| 2015/0327804 A1 | 11/2015 | Lefever et al. | |
| 2015/0358790 A1 | 12/2015 | Nasserbakht | |
| 2016/0038071 A1 | 2/2016 | Williams et al. | |
| 2016/0051847 A1 | 2/2016 | Zhang et al. | |
| 2016/0317044 A1 | 11/2016 | Wu | |
| 2017/0136205 A1 | 5/2017 | Rusher | |
| 2018/0243608 A1 | 8/2018 | Jones et al. | |
| 2018/0318642 A1 | 11/2018 | Lunz et al. | |
| 2018/0339122 A1 | 11/2018 | Lunz et al. | |
| 2018/0341706 A1 | 11/2018 | Agrawal et al. | |
| 2019/0321574 A1* | 10/2019 | Sallee | A61M 16/024 |
| 2019/0336085 A1 | 11/2019 | Kayser et al. | |
| 2020/0086074 A1 | 3/2020 | Rusher | |
| 2020/0155898 A1 | 5/2020 | Kuronen et al. | |
| 2020/0245873 A1 | 8/2020 | Frank et al. | |
| 2020/0279339 A1 | 9/2020 | Akutagawa et al. | |
| 2020/0388287 A1 | 12/2020 | Anushiravani et al. | |
| 2021/0068668 A1 | 3/2021 | Slyusarenko et al. | |
| 2021/0076966 A1 | 3/2021 | Grantcharov et al. | |
| 2021/0290184 A1 | 9/2021 | Ahmed et al. | |
| 2022/0057092 A1 | 2/2022 | Mou et al. | |
| 2022/0192513 A1 | 6/2022 | Atlas | |
| 2022/0331659 A1 | 10/2022 | Chen et al. | |
| 2022/0401672 A1 | 12/2022 | Trumbower et al. | |
| 2023/0041220 A1* | 2/2023 | Iyer | A61B 5/0205 |

FOREIGN PATENT DOCUMENTS

| | | | |
|---|---|---|---|
| WO | WO-2010150264 A1 * | 12/2010 | A61B 5/0816 |
| WO | 2016022974 A1 | 2/2016 | |

OTHER PUBLICATIONS

Notice of Allowance issued on Mar. 27, 2023, in related U.S. Appl. No. 18/076,581, 11 pages.

Office Action issued on Sep. 7, 2023, in related U.S. Appl. No. 18/076,577, 33 pages.

Office Action issued on Dec. 22, 2023, in related U.S. Appl. No. 18/076,577, 22 pages.

* cited by examiner

Setting a target weaning strategy among at least one weaning
strategy, based on at least one input of a user, where the at
least one input corresponds to a clinical decision determined
by the user                                                       201

WEANING METHOD AND RELATED PRODUCTS

TECHNICAL FIELD

The present disclosure relates generally to the technical field of medical technology, and in particular, to a method for assisting a patient in weaning from a therapy and related products.

BACKGROUND

A respiratory disease may be caused by viruses, for example, the COVID-19 virus. A respiratory disease often reduces a patient's oxygen level in blood, resulting in hypoxemia, a condition that damages the heart, brain, and other human organs.

In the current COVID-19 pandemic, oxygen therapy is widely used in medical treatment for patients with respiratory diseases. Assisting a patient in weaning from the oxygen therapy is a crucial element of successful treatment.

This background information is provided to reveal information believed by the applicant to be of possible relevance to the present disclosure. No admission is necessarily intended, nor should be construed, that any of the preceding information constitutes prior art against the present disclosure.

SUMMARY

The present disclosure provides a method for assisting a patient in weaning from a therapy and related products.

An objective of the present disclosure is to reduce the amount of time a healthcare worker needs to be in close contact with a COVID-19 patient during a weaning process, and thus reduce the risk of the healthcare worker being infected by the COVID-19 patient. Another objective of the present disclosure is to reduce human and hospital error.

Medical errors are serious public health problems. Human errors are a major part of medical errors. Weaning involves multiple adjustments to FiO2 and flow rate. Manual adjustments of FiO2 and flow rate increase risks of human errors.

Another objective of the present disclosure is to make timely adjustment to avoid a prolonged weaning process. During a pandemic period, a respiratory therapist may need to attend to many patients, which may result in a delay of weaning adjustment at desired time. A processor using a stored weaning protocol can make FiO2 and flow rate adjustments at the exact time the adjustments need to be made.

One more objective of the present disclosure is to reduce the workload and to increase the working efficiency of caregivers.

A further objective of the present disclosure is to make a small adjustment over the adjustment interval instead of big adjustments. For example, if an adjustment of a weaning protocol is to reduce the flow rate by 5 liters-per-minute every 2 hours, the processor-controlled weaning can reduce the flow rate by 1 liter-per-minute every 20 minutes over 10 hours period. Patients are likely to tolerate smaller changes.

A further objective of the present disclosure is to provide feedback to the caregiver so that the effectiveness of weaning is monitored.

A further objective of the present disclosure is to reduce total weaning time, thus reducing the length of hospital stay. Early discharge from hospitals may significantly reduce the cost of healthcare systems and patients.

A further objective of the present disclosure is to enable weaning to be performed at a long-term care facility or even at patient's home. Performing weaning at a long-term care facility or at home may further reduce cost of healthcare system and a patient.

Another objective of the present disclosure is to make timely adjustments to avoid adverse effects to a patient. When a respiratory therapist reduces the flow rate and/or the FiO2 of the device output, a patient may experience a rapid reduction of SpO2 as a result of the adjustment. Under such a situation, a respiratory therapist needs to reverse the adjustment of the flow rate and/or FiO2. However, a respiratory therapist may not make timely adjustment if he/she is not at the side of the patient to observe the changes, which may result in undesired effect to the patient.

A first aspect of the present disclosure relates to a method for assisting a patient in weaning from a therapy, where the method is executed by a controller, the controller is configurable with at least one weaning strategy, and the method includes:

setting, based on at least one input of a user, a target weaning strategy among the at least one weaning strategy, where the at least one input corresponds to a clinical decision determined by the user.

In a possible implementation, the method further includes:

receiving authentication information input by the user; and determining, according to the authentication information, whether the user has an authority for accessing the at least one weaning strategy.

In a possible implementation, the method further includes:

receiving a physiological parameter of the patient transmitted by at least one measurement device associated with the patient; and adjusting, based on the physiological parameter and the target weaning strategy, a device setting for the therapy.

In a possible implementation, the device setting includes a flow rate and an FiO2 (Fraction of Inspired Oxygen, the concentration of oxygen in the gas mixture) of a gas provided to the patient, and the adjusting, based on the physiological parameter and the target weaning strategy, the device setting for the therapy includes:

determining, based on the physiological parameter and the target weaning strategy, whether the patient is in a target state to obtain a determination result; and adjusting, according to the determination result, at least one of the flow rate and the FiO2 of the gas provided to the patient.

In a possible implementation, the determining, based on the physiological parameter and the target weaning strategy, whether the patient is in a target state to obtain a determination result includes:

determining whether the received physiological parameter of the patient is within a preset physiological parameter range, where the preset physiological parameter range is included in the target weaning strategy;

determining that the patient is in the target state in a case that received physiological parameter of the patient is within the preset physiological parameter range; and determining that the patient is not in the target state in a case that the received physiological parameter of the patient is not within the preset physiological parameter range.

In a possible implementation, the determining, based on the physiological parameter and the target weaning strategy, whether the patient is in a target state to obtain a determination result includes:

calculating a difference value between a value of the received physiological parameter and a reference value included in the target weaning strategy;

determining that the patient is in the target state in a case that the difference value is not greater than a preset value; and determining that the patient is not in the target state in a case that the difference value is greater than the preset value.

In a possible implementation, the determining, based on the physiological parameter and the target weaning strategy, whether the patient is in a target state to obtain a determination result includes:

calculating a percentage that a value of the received physiological parameter deviates from a reference value included in the target weaning strategy;

determining that the patient is in the target state in a case that the percentage is not greater than a second preset value; and determining that the patient is not in the target state in a case that the percentage is greater than the second preset value.

In a possible implementation, the physiological parameter includes a respiratory rate, and in a case that the patient is not in the target state, the method further includes:

determining whether the respiratory rate is greater than a third preset value, where the third preset value is used to determine whether the patient is in a critical state; and outputting an alarm signal in a case that the respiratory rate is greater than the third preset value.

In a possible implementation, the physiological parameter further includes SpO2 (Oxygen Saturation Level, a percentage of oxygen in blood), and the at least one measurement device includes at least one of an oximeter and a respiratory sensor:

where the SpO2 is transmitted by the oximeter associated with the patient, and the respiratory rate is transmitted by the respiratory sensor associated with the patient.

In a possible implementation, the method further includes:

determining whether the flow rate or the FiO2 of the gas provided to the patient satisfies a weaning condition included in the target weaning strategy; and outputting a weaning signal in a case that the flow rate or the FiO2 of the gas provided to the patient satisfies the weaning condition.

In a possible implementation, the weaning condition is that the flow rate of the gas provided to the patient is less than a fourth preset value, and/or the FiO2 of the gas provided to the patient is less than a fifth preset value.

In a possible implementation, the adjusting, based on the physiological parameter and the target weaning strategy, the device setting for the therapy includes:

adjusting, based on the physiological parameter and the target weaning strategy, the device setting for the therapy every preset time interval, where the preset time interval is included in the target weaning strategy.

In a possible implementation, the method further includes: outputting a notification signal in a case that the patient is in the target state, where the notification signal is used to inform the user that the patient is in the target state.

A second aspect of the present disclosure relates to an apparatus for assisting a patient in weaning from a therapy, where the apparatus is configurable with at least one weaning strategy, and the apparatus includes:

a setting module, configured to set a target weaning strategy based on at least one input of a user, where the at least one input corresponds to a clinical decision determined by the user.

In a possible implementation, the apparatus further includes:

a first receiving module, configured to receive authentication information input by the user; and a determining module, configured to determine, according to the authentication information, whether the user has an authority for accessing the at least one weaning strategy.

In a possible implementation, the apparatus further includes:

a second receiving module, configured to receive a physiological parameter of the patient transmitted by at least one measurement device associated with the patient; and an adjusting module, configured to adjust a device setting for a therapy of the patient, based on the physiological parameter and the target weaning strategy.

In a possible implementation, the device setting includes a flow rate and an FiO2 of a gas provided to the patient, and the adjusting module includes:

a determining unit, configured to determine whether the patient is in a target state to obtain a determination result, based on the physiological parameter and the target weaning strategy; and an adjusting unit, configured to adjust, according to the determination result, at least one of the flow rate and the FiO2 of the gas provided to the patient.

In a possible implementation, the determining unit is configured to:

determine whether the received physiological parameter of the patient is within a preset physiological parameter range, where the preset physiological parameter range is included in the target weaning strategy;

determine that the patient is in the target state in a case that the received physiological parameter of the patient is within the preset physiological parameter range; and determine that the patient is not in the target state in a case that the received physiological parameter of the patient is not within the preset physiological parameter range.

In a possible implementation, the determining unit is configured to:

calculate a difference value between a value of the received physiological parameter and a reference value included in the target weaning strategy;

determine that the patient is in the target state in a case that the difference value is not greater than a preset value; and determine that the patient is not in the target state in a case that the difference value is greater than the preset value.

In a possible implementation, the determining unit is configured to:

calculate a percentage that a value of the received physiological parameter deviates from a reference value included in the target weaning strategy;

determine that the patient is in the target state in a case that the percentage is not greater than a second preset value; and determine that the patient is not in the target state in a case that the percentage is greater than the second preset value.

In a possible implementation, the physiological parameter includes a respiratory rate, and in a case that the patient is not in the target state, the determining unit is configured to determine whether the respiratory rate is greater than a third preset value, where the third preset value is used to determine whether the patient is in a critical state:

the apparatus further includes an outputting module, configured to output an alarm signal in a case that the respiratory rate is greater than the third preset value.

In a possible implementation, the physiological parameter further includes SpO2, and the at least one measurement device includes at least one of an oximeter and a respiratory sensor:

where the SpO2 is transmitted by the oximeter associated with the patient, and the respiratory rate is transmitted by the respiratory sensor associated with the patient.

In a possible implementation, the determining module is further configured to determine whether the gas flow rate or the FiO2 of the gas provided to the patient satisfies a weaning condition included in the target weaning strategy;

the outputting module is further configured to output a weaning signal in a case that the flow rate or the FiO2 of the gas provided to the patient satisfies the weaning condition.

In a possible implementation, the weaning condition is that the flow rate of the gas provided to the patient is less than a fourth preset value, and/or the FiO2 of the gas provided to the patient is less than a fifth preset value.

In a possible implementation, the adjusting module is configured to:

adjust, based on the physiological parameter and the target weaning strategy, the device setting for the therapy every preset time interval, where the preset time interval is included in the target weaning strategy.

In a possible implementation, the outputting module is further configured to output a notification signal in a case that the patient is in the target state, where the notification signal is used to inform a user that the patient is in the target state.

A third aspect of the present disclosure relates to a controller, configurable with at least one weaning strategy, where the controller includes:

at least one processor; and a memory communicatively connected with the at least one processor;

where the memory stores instructions executable by the at least one processor, and the instructions, when executed by the at least one processor, cause the at least one processor to:

set a target weaning strategy among the at least one weaning strategy based on at least one input of a user, where the at least one input corresponds to a clinical decision determined by the user.

In a possible implementation, the instructions, when executed by the at least one processor, cause the at least one processor to:

receive authentication information input by the user; and determine, according to the authentication information, whether the user has an authority for accessing the at least one weaning strategy.

In a possible implementation, the instructions, when executed by the at least one processor, cause the at least one processor to:

receive a physiological parameter of a patient transmitted by at least one measurement device associated with the patient; and adjust a device setting for a therapy of the patient, based on the physiological parameter and a target weaning strategy.

In a possible implementation, the device setting includes a flow rate and an FiO2 of a gas provided to the patient, and the instructions, when executed by the at least one processor, cause the at least one processor to:

determine, based on the physiological parameter and the target weaning strategy, whether the patient is in a target state to obtain a determination result; and adjust, according to the determination result, at least one of the flow rate and the FiO2 of the gas provided to the patient.

In a possible implementation, the physiological parameter includes a respiratory rate, and the instructions, when executed by the at least one processor, cause the at least one processor to: in a case that the patient is not in the target state, determine whether the respiratory rate is greater than a third preset value, where the third preset value is used to determine whether the patient is in a critical state; and output an alarm signal in a case that the respiratory rate is greater than the third preset value.

A fourth aspect of the present disclosure relates to a respiratory device which includes the controller, where the controller is configurable with at least one weaning strategy, and the controller includes:

at least one processor; and a memory communicatively connected with the at least one processor;

where the memory stores instructions executable by the at least one processor, and the instructions, when executed by the at least one processor, cause the at least one processor to:

set a target weaning strategy among the at least one weaning strategy based on at least one input of a user, where the at least one input corresponds to a clinical decision determined by the user.

In a possible implementation, the respiratory device further includes a remote terminal, where the controller and the remote terminal are connected communicatively, and the remote terminal is used by the user to import the at least one input for setting the target weaning strategy in a case that the user has an authority for accessing the at least one weaning strategy.

A fifth aspect of the present disclosure relates to a non-transitory computer readable storage medium, storing thereon computer executable instructions which, when being executed by a controller configurable with at least one weaning strategy, implement:

setting, based on at least one input of a user, a target weaning strategy among the at least one weaning strategy, where the at least one input corresponds to a clinical decision determined by the user.

DETAILED DESCRIPTION OF THE EMBODIMENTS

Figures 1, 2:
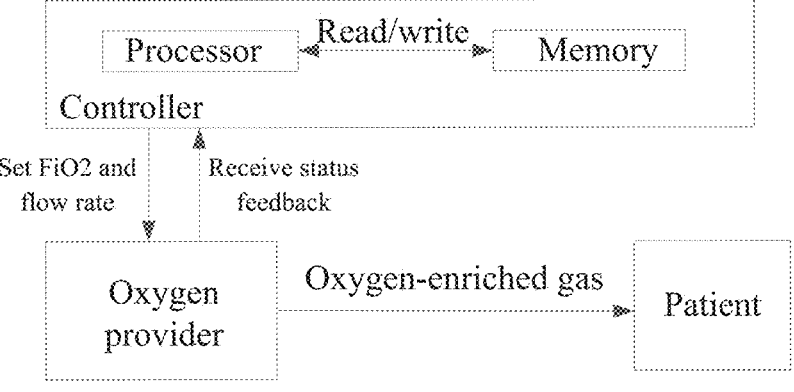
FIG. 1 is a schematic diagram of an application scenario of a method for assisting a patient in weaning from a therapy according to an embodiment of the present disclosure.
FIG. 2 is a flowchart of a method for assisting a patient in weaning from a therapy according to an embodiment of the present disclosure.

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and include structural or logical changes not depicted in the figures. The following detailed description, therefore, is not to be taken in a limiting sense, and the scope of the present disclosure is defined by the appended claims.

For instance, it is understood that a disclosure in connection with a described method may also hold true for a corresponding device or system configured to perform the method and vice versa. For example, if one or a plurality of specific method steps are described, a corresponding device may include one or a plurality of units, e.g., functional units, to perform the described one or plurality of method steps (e.g., one unit performing the one or plurality of steps, or a plurality of units each performing one or more of the plurality of steps), even if such one or more units are not explicitly described or illustrated in the figures. On the other hand, for example, if a specific apparatus is described based on one or a plurality of units, e.g., functional units, a corresponding method may include one step to perform the functionality of the one or plurality of units (e.g., one step performing the functionality of the one or plurality of units, or a plurality of steps each performing the functionality of one or more of the plurality of units), even if such one or plurality of steps are not explicitly described or illustrated in the figures. Further, it is understood that the features of the various exemplary embodiments and/or aspects described herein may be combined with each other, unless specifically noted otherwise.

In the embodiments of the present disclosure, expressions such as "exemplary" or "for example" are used to indicate illustration of an example or an instance. In the embodiments of the present disclosure, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

The term "patient" refers to a person who is the subject to which the methods and/or apparatuses described herein are helping to wean from an oxygen therapy.

The term "physiological parameter" refers to a parameter obtained passively or actively from the patient that is indicative of present physiological state of the patient. The example embodiments herein discuss various examples of physiological parameters that may be employed, however, it is to be appreciated that other physiological parameters may be employed without varying from the scope of the present disclosure.

The term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

The gas provided to a patient may be a mixture of oxygen and air provided by an oxygen provider which may be a device or a system that provides oxygen-enriched gas. For example, an oxygen provider may include a low-pressure oxygen source which generates low-pressure oxygen, an accumulator where the low-pressure oxygen and ambient air are mixed to produce the oxygen-enriched gas, and a blower device to blow the oxygen-enriched gas to a patient. The low-pressure oxygen source may be a concentrator which concentrates the oxygen from ambient air by removing nitrogen selectively to create a high-concentration oxygen gas stream, or a cylinder and a flow regulator, where the cylinder provides high-pressure oxygen and the flow regulator regulates compressed high-pressure oxygen to low-pressure oxygen, or a liquid oxygen supplier and a flow regulator which regulates liquid oxygen to low-pressure oxygen (in gas form).

In oxygen therapy, oxygen provided by an oxygen source is often mixed with air, i.e., blended oxygen and air, so as to produce oxygen-enriched gas suitable to achieve a therapeutic fraction ratio of inspired oxygen (FiO2). The oxygen-enriched gas of a certain FiO2 is delivered to a patient via an airway tube and a patient interface, for example, a nasal cannula, a mask, or a tracheostomy adaptor.

In addition, the term "room air" refers to the gas for regular breathing, which includes 21% oxygen, without supplemental oxygen.

As described in the background, in related art, assisting a patient in weaning from an oxygen therapy is a crucial element of successful treatment.

In hospitals today, patients are weaned from high flow therapy manually by respiratory therapists. This process is not uniform and may or may not have a written protocol. The written protocol is related to a weaning strategy. When weaning, the respiratory therapist will lower the gas flow rate and/or the FiO2 percentage at set time intervals and then assess the patient response to this weaning by observing the effect on SpO2 and Respiratory Rate.

If the patient maintains or shows minimal change in SpO2 levels and Respiratory Rate, the respiratory therapist will then continue lowering the two device settings until such time as the patient can be moved to simple oxygen cannula (e.g., 6 lpm 100% FiO2 or lower) or transition to room air only (i.e., regular breathing). In general, there are five methods: a). flow rate reduction first, b). FiO2 reduction first, c). simultaneous (flow rate and FiO2) reduction d). alternative reduction with flow rate reduction first and FiO2 reduction second, and e). alternative reduction with FiO2 reduction first and flow rate reduction second.

If the patient shows negative changes in SpO2 (lower) and/or Respiratory Rate (higher), the patient will be raised to the previous level where, if stabilized, the weaning will be attempted again. If the patient continues to show negative changes in SpO2 and/or Respiratory Rate, the patient will be further escalated and the weaning trial may be aborted.

In terms of patients infected by contagious virus such as COVID-19, a manual operation, i.e., manual adjustment of flow rate and FiO2 will expose a respiratory therapist to a risk of being infected.

Finer steps (meaning reduction of FiO2 and flow rate in finer intervals: more frequent changes in shorter time intervals) of a weaning strategy may be more beneficial to a patient. However, finer steps may require more frequent visits of a respiratory therapist (RT) in the current manual weaning operation, adding to the requirement of RT resources (adding the workload such as time, attention of the respiratory therapist), and the cost of patients and the cost of healthcare systems.

Based on this conventional method with manual operation, a respiratory therapist cannot track the physiological symptoms of a patient in real time, or may not be able to track the patient's conditions as frequently as desired. As a result, the adverse changes of the patient during the weaning process may not be handled in a timely manner.

A method for assisting a patient in weaning from a therapy is described in the present disclosure. The aim of the solution provided in the present disclosure is to assist a patient in weaning from a therapy in a semi-automatic or fully automatic manner, which is a low-risk and real-time weaning method, which enables finer steps of a weaning strategy, timely response to the patient conditions, less frequent visit to the patients by a respiratory therapist, less risk of cross infection by the patient to a respiratory therapist, and less cost to the patients and the healthcare systems.

FIG. 1 is a schematic diagram of an application scenario of a method for assisting a patient in weaning from a therapy according to an embodiment of the present disclosure. As shown in FIG. 1, a controller is communicatively connected to an oxygen provider, the controller includes communicatively connected processor and memory, and the oxygen provider is capable of delivering oxygen-enriched gas via a gas pathway from the oxygen provider side to a patient side. The memory may store multiple weaning strategies. The controller may be configured with at least one weaning strategy, and the controller may set, based on at least one input of a user (e.g., a respiratory therapist, a doctor, a nurse), a target weaning strategy among the at least one weaning strategy, where the at least one input corresponds to a clinical decision determined by the user. Further, the controller may, based on the set target weaning strategy, control the oxygen provider which provides oxygen-enriched gas to the patient, thereby adjusting a device setting for the therapy of the patient, where the device setting may be configuration of the oxygen provider and may include a flow rate or FiO2 of the oxygen-enriched gas (also referred to supplemental oxygen or blended oxygen and air) provided to the patient. The controller may also receive status feedback from the oxygen provider. Thus, a semi-automatic weaning method executed by a controller is achieved, which can effectively reduce the risk of being infected and reduce the workload of the respiratory therapist, and is a low risk, high impact way to customize and implement the process. In addition, the present disclosure enables the timely handling of patient situations, which in turn reduces the risk of potential adverse effects on patients.

It is understood that FIG. 1 is merely a logical schematic diagram, and in a practical application scenario, the function components may be implemented in various forms. For example, the controller may be integrated into the oxygen provider as a hardware/software/firmware unit of the oxygen provider, the integrated device may also be referred to as a respiratory device. It should be noted that the method for assisting a patient in weaning from a therapy is not limited to the treatment of the respiratory disease, but can also be used for other diseases, such as muscle fatigue, hypoxemia.

The application scenario of the embodiment of the present disclosure described above is only illustrative, and other application scenarios may also be employed, which is not limited in the embodiments of the present disclosure.

FIG. 2 is a flowchart of a method for assisting a patient in weaning from a therapy according to an embodiment of the present disclosure. The method may be executed by the controller shown in FIG. 1, and the controller is configurable with at least one weaning strategy, that is, at least one weaning strategy can be configured in the controller by a user (e.g., a respiratory therapist) of the controller, the controller simply acts as a tool for automatically implementing the weaning strategy set by the user. More specifically, there may be different weaning strategies for different patients in a hospital, and there may also be different weaning strategies for different hospitals. A respiratory therapist or a respiratory department of a hospital may specify a weaning strategy for a specific patient or a kind of patients, and input the weaning strategy into the controller for assisting a patient in weaning from a therapy. Alternatively, a respiratory therapist or a respiratory department of a hospital may also specify various different weaning strategies and input them into the controller, and when it is required to assist a patient in weaning from a therapy, a respiratory therapist may select one of the weaning strategies according to the condition of the patient.

In a specific implementation, for different respiratory therapists, there may be various different weaning strategies which may be input into the controller, and when it is required to assist a patient in weaning from a therapy, the respiratory therapist in charge of treatment may select a weaning strategy that is constructed by himself, according to the condition of the patient.

In an implementation, the controller may receive authentication information input by a respiratory therapist and determine, according to the authentication information, whether the respiratory therapist has an authority for accessing the at least one weaning strategy. For example, there may be different IDs (e.g., the names of respiratory therapists) and corresponding passwords preset for respiratory therapists, and a respiratory therapist may input his own ID and password, or use biometric authentication (e.g., fingerprint), to authenticate that he has the authority for accessing the weaning strategies associated with the controller, thereby improving the security of the weaning strategies.

When the authentication is successful, i.e., the respiratory therapist has the authority for accessing the weaning strategies, the respiratory therapist can select a weaning strategy according to the condition of a patient from the weaning strategies. The respiratory therapist can also set up and modify the selected weaning strategy, for example, set up or modify a threshold at which the controller outputs an alarm signal to inform the respiratory therapist the adverse condition of a patient.

It should be noted that weaning is a step-by-step process. For example, when the respiratory therapist determines that the patient is in a condition whereas weaning attempt can be implemented, the first adjusting to the device setting for therapy is performed, which may be implemented by the controller upon receiving a start instruction from the respiratory therapist. In an implementation, the first adjusting may be lower the flow rate and/or the FiO2 of the gas provided to the patient. In response to the first adjusting, the patient may output changes in physical condition, which may be reflected by physiological parameters of the patient.

The method described in the embodiment of the present disclosure may include step 201: setting a target weaning strategy among at least one weaning strategy, based on at least one input of a user, where the at least one input corresponds to a clinical decision determined by the user.

Where the user may be a respiratory therapist, and the at least one input includes, but not limited to, a time interval of adjusting the device setting for the therapy (e.g., the flow rate or FiO2 of the gas provided to the patient), an adjusting granularity (e.g., an adjusting percentage of the flow rate or FiO2 each time), a percentage threshold of physiological parameter that deviates from a reference value of a patient (based on which it can be determined that the patient is in a target state or not), a threshold of physiological parameter that deviates from a reference value of a patient (based on which it can be determined that the patient is in a critical state or not), a reference respiratory rate value of a patient indicative of a target state, a weaning condition (e.g., when the flow rate of the oxygen-enriched gas is less than a certain value), etc.

A data structure of a weaning strategy (weaning protocol) is shown below, which lists some exemplary settings that are included in a target weaning strategy and can be modified by a user.

| | |
|---|---|
| Adjusting Frequency | Wean every hour |
| Rules | FiO2 first/Flow rate first/ Simultaneous |
| Adjusting amount | FiO2 1% Flow Rate 1 LPM |
| Max respiratory rate | 30 breaths per minute |
| Minimum SpO2 | 90% |
| Goal | FiO2 <25% Flow Rate <3 LPM |

Figure 3A:
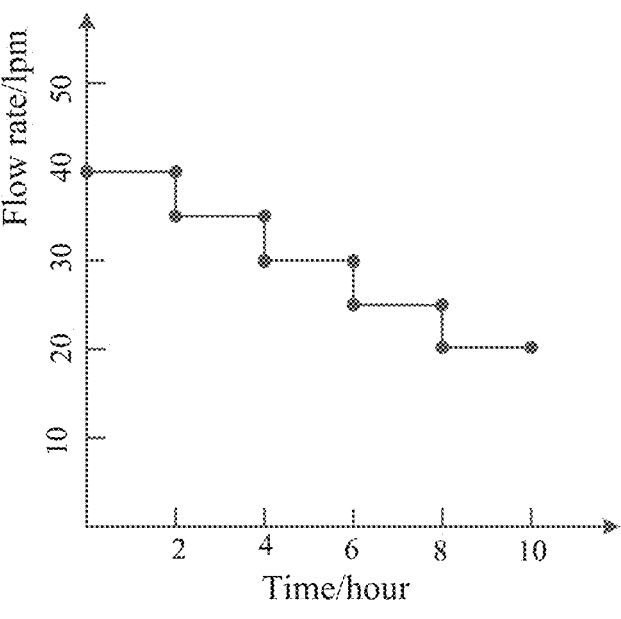
FIG. 3A and FIG. 3B are schematic diagrams each showing an interface for setting a weaning strategy visually according to an embodiment of the present disclosure.
Figure 3B:
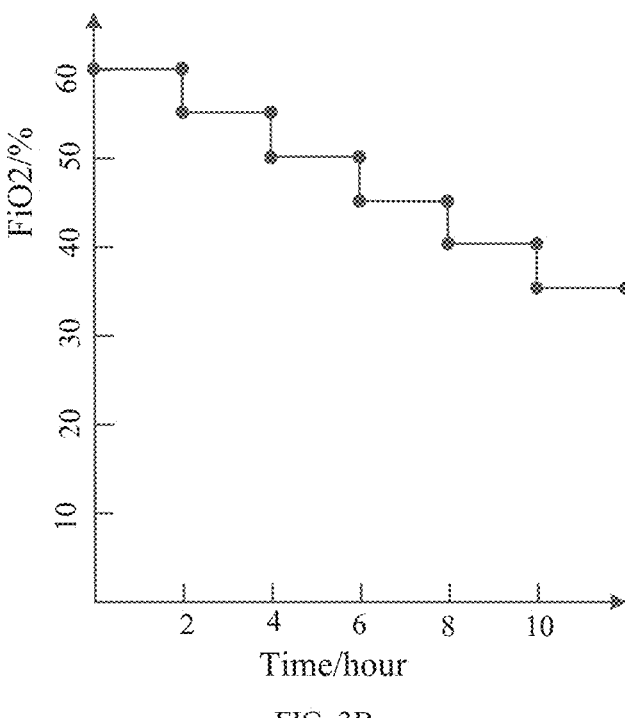

In an implementation, the interface for setting the weaning strategy may be presented in a visual way. FIG. 3A and FIG. 3B are schematic diagrams each showing an interface for setting a weaning strategy visually according to an embodiment of the present disclosure. In the implementation, a respiratory therapist may set the weaning strategy by clicking or adjusting the point or line in the figure. In another implementation, there may be an interface through which the respiratory therapist can modify the values for setting the weaning strategy.

In a specific implementation, the controller may receive a physiological parameter of the patient transmitted by at least one measurement device associated with the patient. The physiological parameter may include at least one of an oxygen saturation level in blood, SpO2; a respiratory rate; and a carbon dioxide level at the end of exhalation, EtCO2. The physiological parameters are measurements obtained from measurement devices or sensors. The SpO2 may be transmitted to the controller by an oximeter attached to the patient, the respiratory rate may be transmitted to the controller by a respiratory sensor (e.g., a pressure sensor on a nasal cannula, a wearable pressure sensor, or a wearable motion sensor) associated with the patient, the EtCO2 may be transmitted to the controller by a gas sensor in the patient's exhalation pathway.

A sensor in the exhalation pathway can have a combined sensor to measure both respiratory rate and EtCO2. A wearable sensor can measure SpO2, respiratory rate, or EtCO2, or any combination of SpO2, respiratory rate, and EtCO2.

For example, an oximeter, a respiratory sensor and a gas sensor may respectively be connected to the patient and obtain SpO2, the respiratory rate and the EtCO2, respectively. The oximeter, the respiratory sensor and the gas sensor may, through a wired or wireless manner, transmit the obtained SpO2, respiratory rate and EtCO2 to the controller, respectively. Correspondingly, the controller receives the SpO2, respiratory rate and EtCO2 transmitted by the oximeter, the respiratory sensor and the gas sensor, respectively.

It should be understood that the physiological parameter may include other indicators of the patient, and the controller may receive those other indicators from corresponding measurement devices in a case that the indicators are required for determining the state of the patient, which is not limited in the embodiment of the present disclosure.

In an implementation, the controller may adjust a device setting for the therapy, based on the physiological parameter and the target weaning strategy. The device setting may include a flow rate and an FiO2 of a gas (oxygen-enriched gas) provided to the patient. The controller may determine whether the patient is in a target state to obtain a determination result, based on the physiological parameter and the target weaning strategy. According to the determination result, the controller may adjust at least one of the flow rate and the FiO2 of the gas provided to the patient. The target state may be a stable state of the patient. In a case that the patient is in the target state, the controller may output a notification signal, where the notification signal is used to inform a user, e.g., a respiratory therapist, that the patient is in the target state. In another implementation, the device setting may also include humidity and temperature of the gas provided to the patient.

In a specific implementation, the controller may determine whether the received physiological parameter of the patient is within a preset physiological parameter range, e.g., a preset SpO2 range, a preset respiratory rate range. For example, a preset SpO2 range for a patient under treatment maybe 89%~92%. The preset physiological parameter range may be included in the target weaning strategy and may be set according to actual needs by a hospital or a respiratory therapist in a hospital. Then the controller may determine that the patient is in the target state in a case that the received physiological parameter of the patient is within the preset physiological parameter range. And the controller may determine that the patient is not in the target state in a case that the received physiological parameter of the patient is not within the preset physiological parameter range.

For example, in a case that the received SpO2 of the patient is within the preset SpO2 range and the received respiratory rate of the patient is within the preset respiratory rate range, it is determined that the patient is in the target state. Otherwise, it is determined that the patient is not in the target state.

In another specific implementation, the controller may calculate a difference value between a value of the received physiological parameter and a reference value, e.g., a different value between a value of the received respiratory rate of the patient and a reference respiratory rate value. The reference respiratory rate value may be included in the target weaning strategy and may be set by the hospital or the respiratory therapist in the hospital, according to the specific condition of the patient. Then the controller may determine that the patient is in a target state in a case that the difference value is not greater than a preset value. And the controller may determine that the patient is not in a target state in a case that the difference value is greater than the preset value.

For example, in a case that the difference value between the value of the received respiratory rate of the patient and the reference respiratory rate value is not greater than the preset value, it can be determined that the patient is in the target state. Otherwise, it is determined that the patient is not in the target state.

In yet another specific implementation, the controller may calculate a percentage that a value of the received physiological parameter deviates from a reference value, e.g., a percentage that a value of the received respiratory rate of the patient deviates from a reference respiratory rate value. The reference respiratory rate value may be included in the target weaning strategy and may be set by the hospital or the respiratory therapist in the hospital, according to the specific condition of the patient. Then the controller may determine that the patient is in the target state in a case that the percentage is not greater than a second preset value. And the controller may determine that the patient is not in the target state in a case that the percentage is greater than the second preset value.

For example, in a case that the percentage that the value of the received respiratory rate of the patient deviates from the reference respiratory rate value is not greater than the second preset value, it is determined that the patient is in the target state. Otherwise, it is determined that the patient is not in the target state.

In response to the determination that the patient is in the target state, the controller may reduce the flow rate and the FiO2 of the gas provided to the patient at the same time, and may also reduce one of the flow rate and the FiO2 while increasing the other. In response to the determination that the patient is not in the target state, the controller may increase the flow rate and the FiO2 of the gas provided to the patient at the same time, and may also increase one of the flow rate and the FiO2 while reducing the other. For example, if it is determined that the patient is in the target state and there is residual gas in the patient's respiratory tract, the flow rate can be increased to bring the residual gas out, and FiO2 can be reduced at this time.

In an implementation, after adjusting at least one of the flow rate and the FiO2 of the gas provided to the patient, the controller may continue to receive the physiological parameter of the patient such as the SpO2 and the respiratory rate of the patient in real time. If the physiological parameter shows that the patient is in a target state for a period of time, for example, for five minutes, it is determined that the condition of the patient is stable, upon which the gas provided to the patient can be adjusted again.

In addition, after determining that the patient is not in the target state, it may be further determined whether the respiratory rate of the patient is greater than a third preset value. This value may be set in the target weaning strategy in advance and is used to determine whether the patient is in a critical state, and this value may be, for example, 24 breaths per minute for an adult. In a case that the respiratory rate of the patient is greater than the third preset value, the controller outputs an alarm signal. The alarm signal may be a flashing light or a bell for informing the respiratory therapist that the patient is in a critical state. Upon receiving the alarm signal, the respiratory therapist may consider intubating the patient. In addition, in a case that the respiratory rate is greater than the third preset value, the controller may send a notification signal to a remote terminal or an APP integrated therein, or other devices that may be tracking the physiological parameter of the patient. In an implementation, there may be a camera set around the patient, which can take a picture of the current state of the patient and send the picture to a remote terminal or an APP integrated therein, or other devices that may be tracking the physiological state of the patient.

In an implementation, the adjusting step may be performed every preset time interval, and the preset time interval may also be included in the target weaning strategy and may be set according to actual needs. The preset time interval may be five minutes. After several times adjusting the gas provided to the patient, the controller may output a signal to inform the respiratory therapist that the adjusting has been performed by, for example, 5%. At the same time, the controller may output a prompt like "Would you like to continue weaning?". Then the controller may receive from the respiratory therapist an instruction indicating whether to continue the adjusting step or not. Alternatively, there may be a relatively great adjusting threshold (e.g., 5%) in the target weaning strategy, and when it is to adjust such great extent of the gas provided to patient, the controller may output a signal to inform the respiratory therapist and receive from the respiratory therapist an instruction indicating whether to continue to adjust such great extent of the gas provided to the patient. In addition, after determining that the physiological parameter of the patient remains in a target range for a period of time, such as 20 minutes, the controller may also output a notification that the patient has been in the target state for the time established in the weaning strategy and is now ready for the next step in the weaning with a prompt like "Would you like to continue weaning?". Alternatively, the controller may not output any information to the respiratory therapist during an entire weaning process but instead adjust automatically every preset time interval if the physiological parameter of the patient has remained in the target range, according to a complete weaning strategy set in advance.

In a specific implementation, a respiratory therapist may set a weaning condition in the target weaning strategy in advance, for example, before executing the weaning method by the controller. Setting the weaning condition may be setting a threshold of the device setting, e.g., a threshold of the flow rate and a threshold of the FiO2 of the gas provided to the patient, less than which it is determined that the patient can be weaned from the oxygen therapy. In an implementation, the weaning condition may be, for example, the flow rate of the gas provided to the patient is less than a fourth preset value (e.g., 10 lpm), and/or the FiO2 of the gas provided to the patient is less than a fifth preset value (e.g., 50%).

After several times adjusting the gas provided to the patient, the flow rate or the FiO2 of the gas provided to the patient may satisfy the weaning condition, at which time the controller may output a weaning signal. The weaning signal may inform the respiratory therapist that the patient can be moved to a simple oxygen cannula (e.g., 6 lpm 100% FiO2 or lower) or transition to room air only (i.e., regular breathing).

Figure 4:
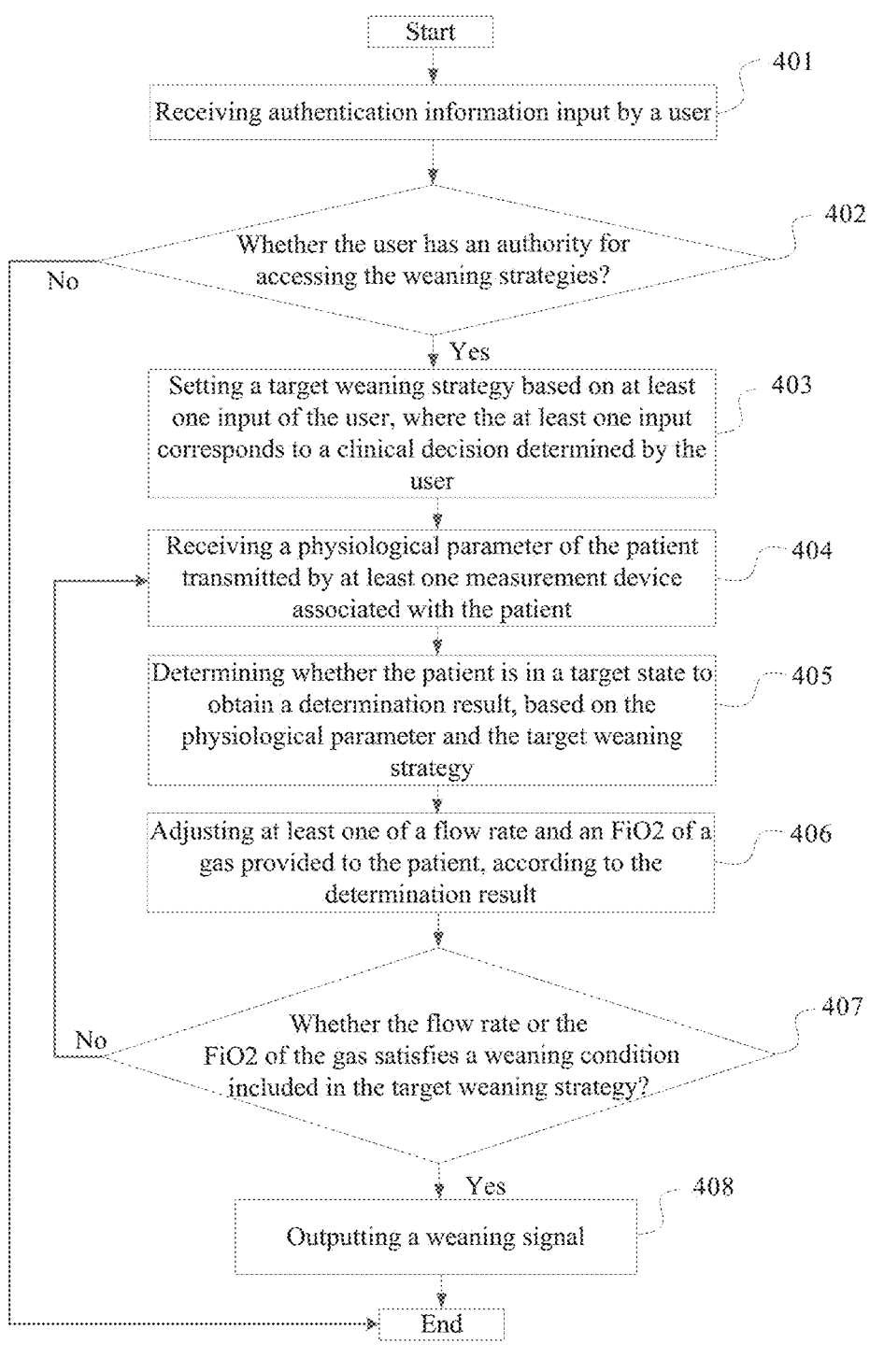
FIG. 4 is a flowchart of a method for assisting a patient in weaning from a therapy according to an embodiment of the present disclosure.

FIG. 4 is a flowchart of a method for assisting a patient in weaning from a therapy according to an embodiment of the present disclosure. As shown in FIG. 4, the method includes the following steps.

Step 401, receiving authentication information input by a user.

Step 402, determining whether the user has an authority for accessing the weaning strategies, according to the authentication information.

Step 403, setting a target weaning strategy based on at least one input of the user, where the at least one input corresponds to a clinical decision determined by the user.

Step 404, receiving a physiological parameter of the patient transmitted by at least one measurement device associated with the patient.

Step 405, determining whether the patient is in a target state to obtain a determination result, based on the physiological parameter and the target weaning strategy.

Step 406, adjusting, according to the determination result, at least one of a flow rate and an FiO2 of a gas provided to the patient.

Step 407, determining whether the flow rate or the FiO2 of the gas satisfies a weaning condition included in the target weaning strategy. If yes, perform step 408; and if no, return back to step 404.

Step 408, outputting a weaning signal.

The weaning signal is used to inform the respiratory therapist that the patient can be moved to a simple oxygen cannula (e.g., 6 lpm 100% FiO2 or lower) or transition to room air only (i.e., regular breathing).

Figure 5:
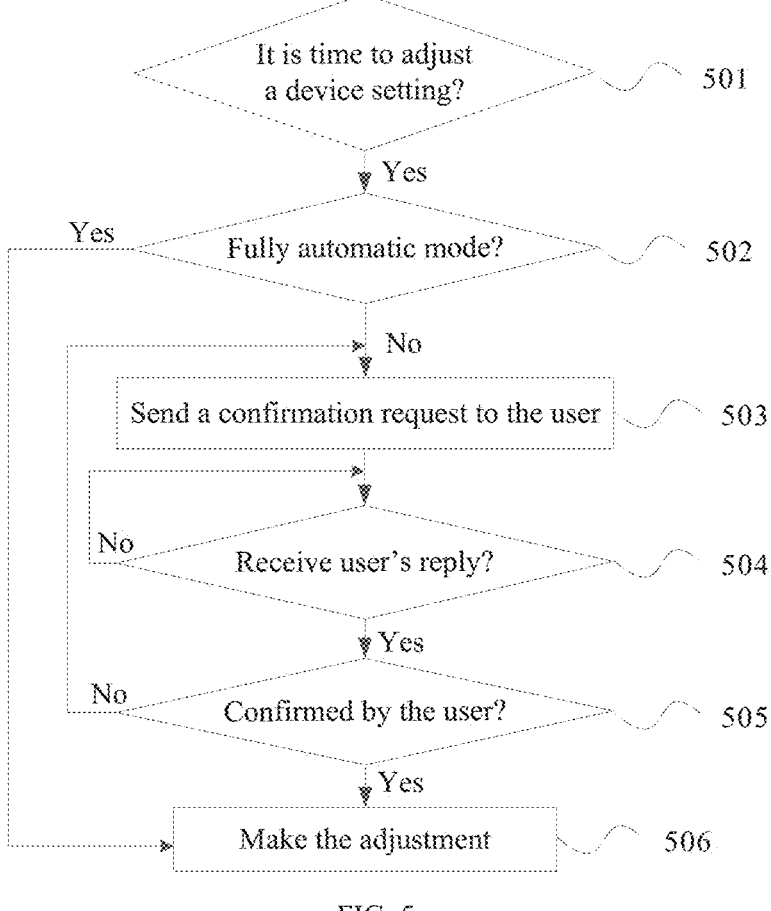
FIG. 5 is a flowchart showing operations in semi-automatic mode and fully automatic mode according to an embodiment of the present disclosure.

FIG. 5 is a flowchart showing operations in semi-automatic mode and fully automatic mode according to an embodiment of the present disclosure. As shown in FIG. 5, a semi-automatic mode only implementation uses the first and the last four steps and a fully automatic mode only implementation uses the first two and the last steps. Specifically, when it is time to adjust a device setting (501), the controller may determine whether the operation mode is a fully automatic mode (502), and in a case that the operation mode is a fully operation mode, the controller makes the adjustment automatically (506). In a case that the operation mode is not a fully operation mode, the controller determines that the operation mode is a semi-automatic mode and send a confirmation request to the user (503). The controller may continuously monitor the user's reply (504), and determine whether it is confirmed by the user after receiving the user's reply (505). In a case that it is confirmed by the user, the controller makes the adjustment (506).

In a possible implementation, the controller has three operation modes: a manual mode, a semi-automatic mode, and a fully automatic mode. In a manual mode, a user manually adjusts the device settings such as the flow rate and the FiO2. The controller uses those device settings to control the gas provided to the patient. In a semi-automatic mode, the controller sends a message, e.g., a confirmation request, to the user when it is ready to adjust at least one of the flow rate and the FiO2 according to a weaning strategy to request a confirmation from the user. After it receives the confirmation, the controller adjusts the device settings to change the gas provided to the patient. In a fully automatic mode, when it is time to adjust those device settings, the controller automatically adjusts the device settings according to the weaning strategy by changing at least one of the flow rate or the FiO2 of the gas provided to the patient.

Figure 6:
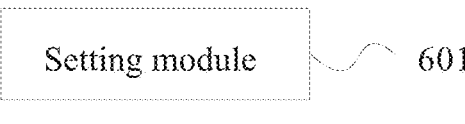
FIG. 6 is a schematic block diagram of an apparatus for assisting a patient in weaning from a therapy according to an embodiment of the present disclosure.

FIG. 6 is a schematic block diagram of an apparatus for assisting a patient in weaning from a therapy according to an embodiment of the present disclosure. As shown in FIG. 6, the apparatus for assisting a patient in weaning from a therapy in the embodiment is configurable with at least one weaning strategy, and the apparatus includes: a setting module 601, configured to set a target weaning strategy based on at least one input of a user, where the at least one input corresponds to a clinical decision determined by the user.

In a possible implementation, the apparatus further includes: a first receiving module, configured to receive authentication information input by the user; and a determining module, configured to determine, according to the authentication information, whether the user has an authority for accessing weaning strategies.

In a possible implementation, the apparatus further includes: a second receiving module and an adjusting module. The second receiving module is configured to receive a physiological parameter of the patient transmitted by at least one measurement device associated with the patient, and the adjusting module is configured to adjust a device setting for the therapy, based on the physiological parameter and the target weaning strategy.

In a possible implementation, the device setting includes a flow rate and an FiO2 of a gas provided to the patient, and the adjusting module includes: a determining unit, configured to determine whether the patient is in a target state to obtain a determination result, based on the physiological parameter and the target weaning strategy; and an adjusting unit, configured to adjust, according to the determination result, at least one of the flow rate and the FiO2 of the gas provided to the patient.

In a possible implementation, the determining unit is configured to: determine whether the received physiological parameter of the patient is within a preset physiological parameter range. The preset physiological parameter range is included in the target weaning strategy; determine that the patient is in the target state in a case that the received physiological parameter of the patient is within the preset physiological parameter range; and determine that the patient is not in the target state in a case that the received physiological parameter of the patient is not within the preset physiological parameter range.

In a possible implementation, the determining unit is configured to: calculate a difference value between a value of the received physiological parameter and a reference value included in the target weaning strategy; determine that the patient is in the target state in a case that the difference value is not greater than a preset value; and determine that the patient is not in the target state in a case that the difference value is greater than the preset value.

In a possible implementation, the determining unit is configured to: calculate a percentage that a value of the received physiological parameter deviates from a reference value included in the target weaning strategy; determine that the patient is in the target state in a case that the percentage is not greater than a second preset value; and determine that the patient is not in the target state in a case that the percentage is greater than the second preset value.

In a possible implementation, the physiological parameter includes a respiratory rate, and in a case that the patient is not in the target state, the determining unit is configured to determine whether the respiratory rate is greater than a third preset value, where the third preset value is used to determine whether the patient is in a critical state. The apparatus further includes an outputting module, configured to output an alarm signal in a case that the respiratory rate is greater than the third preset value.

In a possible implementation, the physiological parameter further includes SpO2, and the at least one measurement device includes an oximeter and a respiratory sensor: where the SpO2 is transmitted by the oximeter associated with the patient, and the respiratory rate is transmitted by the respiratory sensor associated with the patient.

In a possible implementation, the determining module is further configured to determine whether the gas flow rate or the FiO2 of the gas provided to the patient satisfies a weaning condition included in the target weaning strategy. The outputting module is further configured to output a weaning signal in a case that the flow rate or the FiO2 of the gas provided to the patient satisfies the weaning condition.

In a possible implementation, the weaning condition is that the flow rate of the gas provided to the patient is less than a fourth preset value, and/or the FiO2 of the gas provided to the patient is less than a fifth preset value.

In a possible implementation, the adjusting module is configured to: adjust, based on the physiological parameter and the target weaning strategy, the device setting for the therapy every preset time interval, where the preset time interval is included in the target weaning strategy.

In a possible implementation, the outputting module is further configured to output a notification signal in a case that the patient is in the target state, where the notification signal is used to inform a user that the patient is in the target state.

The apparatus for assisting a patient in weaning from a therapy in the embodiment may perform the technical solutions of the method embodiments shown in FIG. 2 to FIG. 5, and the implementation principle and technical effects thereof are similar, and details are not described herein.

Figure 7:
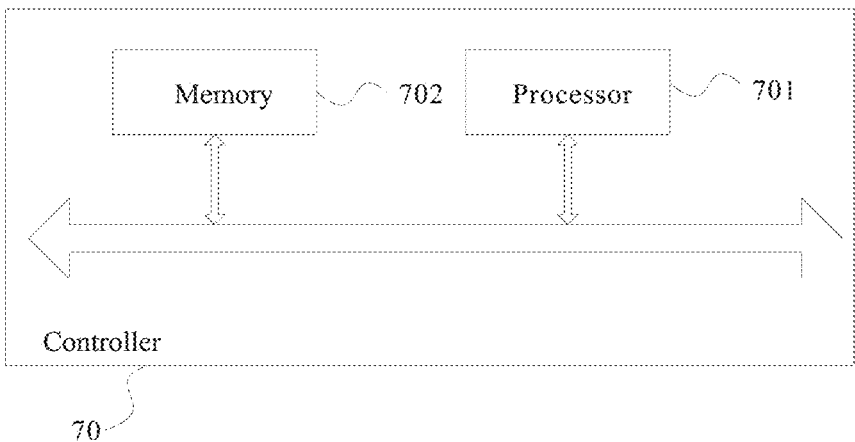
FIG. 7 is a schematic structural diagram of a controller according to an embodiment of the present disclosure.

FIG. 7 is a schematic structural diagram of a controller 70 according to an embodiment of the present disclosure. As shown in FIG. 7, the controller in the embodiment includes: at least one processor 701; and a memory 702 communicatively connected with the at least one processor 701.

The memory 702 stores instructions executable by the at least one processor 701, and the instructions, when executed by the at least one processor 701, cause the at least one processor 701 to implement the methods for assisting a patient in weaning from a therapy according to the embodiments of the present disclosure.

The controller will allow for the inputting of auto-weaning algorithm that will decrease gas flow rate and/or FiO2 percentage at set time intervals. The closed loop algorithm will then have the ability execute the set algorithm using the input settings and will utilize real time sensing of patient parameters (e.g., SpO2, Respiratory Rate, etc.) to determine the effectiveness of the weaning process and adjust accordingly.

Because the particulars of this process are specific to each institution, the controller can be programmed to execute the institution's specific protocol. This will be done during the evaluation process so that the key clinical leaders at each institution can have input on the set protocol. Should this protocol change at the institution, this algorithm can be modified in the future by having the representative return to the site and reprogram the algorithm. The protocol is related to a weaning strategy.

The weaning process for high flow consumes much respiratory therapist time and attention. Often times, other priorities end up delaying the continuance of successful weaning due to lack of an available respiratory therapist. This same lack of attention does not negatively affect the patients because those patients put into weaning protocols/ strategies are stable and closely monitored since the risk associated with weaning is low, as the signs of weaning unsuccessfully (drop in SpO2 and elevation of Respiratory Rate) are easily observable and actioned by other clinicians (e.g., nursing). A device or a controller designed to automate this task would thus allow for a respiratory therapist to not only more efficiently wean patients, but also wean more patients simultaneously, while not creating additional risk to the patient due to current monitoring.

The related description can be understood by referring to the related descriptions corresponding to FIG. 2 to FIG. 5, and details are not described herein.

The present disclosure also provides a respiratory device which includes the controller described above. In an implementation, the respiratory device may further include a remote terminal, where the controller and the remote terminal are connected communicatively. The remote terminal can receive authentication information input by the user and determine whether the user has an authority for accessing the weaning strategies. In a case that the user has the authority for accessing the weaning strategies, the remote terminal can be used by the user to import the at least one input for setting the target weaning strategy. In an implementation, the remote terminal may also be used to store the weaning strategies, and in a case that the user has the authority, the user may access the weaning strategies directly from the remote terminal and set the target weaning strategy.

The present disclosure also provides a non-transitory computer readable storage medium, storing thereon computer executable instructions which, when being executed by a controller configurable with at least one weaning strategy, implement the method for assisting a patient in weaning from a therapy according to embodiments of the present disclosure.

The related description can be understood by referring to the related descriptions corresponding to FIG. 2 to FIG. 5, and details are not described herein.

Terms such as "first", "second" and the like in the specification and claims of the present disclosure as well as in the above drawings are intended to distinguish different objects, but not intended to define a particular order.

The term "a" or "an" is not intended to specify one or a single element, instead, it may be used to represent a plurality of elements where appropriate.

In one or more examples, the functions described may be implemented in hardware, software, firmware, or any combination thereof. For example, the functions may be implemented by one or more processors, such as one or more application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, the techniques could be fully implemented in one or more circuits or logic elements.

In the claims, the word "including" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate, preclude or suggest that a combination of these measures cannot be used to advantage.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. Those embodiments with various modifications are within the range and scope of the following claims.

What is claimed is:

1. A method for assisting a patient in weaning from a therapy, wherein the method is executed by a controller comprising a memory, and the method comprises:

receiving, by the controller before the therapy, multiple weaning strategies inputted into the controller;

storing, by the controller, the multiple weaning strategies into the memory;

receiving, by the controller during the therapy, at least one input of a user, wherein the at least one input corresponds to a clinical decision determined by the user and is used for selecting a target weaning strategy among the multiple weaning strategies stored in the memory, and the at least one input of the user comprises: a time interval of adjusting a flow rate and a FiO2 of a gas provided to the patient; and an adjusting granularity for adjusting the flow rate and the FiO2 of the gas provided to the patient;

setting, by the controller, the target weaning strategy selected from the multiple weaning strategies, based on the time interval of adjusting the flow rate and the FiO2 of the gas provided to the patient and the adjusting granularity for adjusting the flow rate and the FiO2 of the gas provided to the patient;

receiving, by the controller, a physiological parameter of the patient transmitted by at least one measurement device associated with the patient;

calculating, by the controller, a percentage that a value of the received physiological parameter deviates from a reference value comprised in the set target weaning strategy;

determining, by the controller, that a condition of the patient is stable in a case that the percentage is not greater than a second preset value;

determining, by the controller, that the condition of the patient is not stable in a case that the percentage is greater than the second preset value;

adjusting, by the controller according to whether the condition of the patient is stable, the flow rate and the FiO2 of the gas provided to the patient, based on the time interval of adjusting the flow rate and the FiO2 of the gas provided to the patient and the adjusting granularity for adjusting the flow rate and the FiO2 of the gas provided to the patient; and outputting a weaning signal in a case that the flow rate of the gas provided to the patient is less than 10 litre per minute or the FiO2 of the gas provided to the patient is less than 50%, wherein the weaning signal is used to inform the user that the patient can be weaned from the therapy;

wherein the physiological parameter comprises a respiratory rate, and, in a case that the condition of the patient is not stable, the method further comprises:

determining whether the respiratory rate is greater than a third preset value, wherein the third preset value is used to determine whether the patient is in a critical state; and outputting an alarm signal in a case that the respiratory rate is greater than the third preset value.

2. The method according to claim 1, wherein the physiological parameter further comprises SpO2, and the at least one measurement device comprises at least one of an oximeter and a respiratory sensor;

wherein the SpO2 is transmitted by the oximeter associated with the patient, and the respiratory rate is transmitted by the respiratory sensor associated with the patient.

3. The method according to claim 1, wherein the adjusting, by the controller according to whether the condition of the patient is stable, the flow rate and the FiO2 of the gas provided to the patient comprises:

adjusting, by the controller according to whether the condition of the patient is stable, the flow rate and the FiO2 of the gas provided to the patient every preset time interval.

4. The method according to claim 1, further comprising: outputting a notification signal in a case that the condition of the patient is stable, wherein the notification signal is used to inform the user that the condition of the patient is stable.

5. The method according to claim 1, wherein before setting, by the controller, the target weaning strategy selected from the multiple weaning strategies, the method further comprises:

determining one weaning strategy in the multiple weaning strategies stored in the memory to be the target weaning strategy.

6. The method according to claim 1, wherein, the multiple weaning strategies differ from each other by at least one of the following:

adjusting frequency;

a rule for reducing the FiO2 first, or reducing the flow rate first, or reducing the FiO2 and the flow rate simultaneously;

an adjusting amount of the FiO2, an adjusting amount of the flow rate;

a max respiratory rate; and a minimum SpO2.

7. The method according to claim 1, wherein the multiple weaning strategies are inputted into the controller by different users.

8. The method according to claim 7, wherein the at least one input of the user is used for selecting, among the multiple weaning strategies stored in the memory, a first weaning strategy which is inputted into the controller by the user.

9. The method according to claim 7, wherein the at least one input of the user is used for selecting, among the multiple weaning strategies stored in the memory, a second weaning strategy which is inputted into the controller by a different user.

10. The method according to claim 1, wherein the at least one input of the user used for selecting the target weaning strategy among the multiple weaning strategies further comprises:

the second preset value;

a threshold of the physiological parameter that deviates from a second reference value of the patient based on which it can be determined that the patient is in the critical state or not; and a reference respiratory rate value of the patient indicative of the condition of the patient being stable.

11. The method according to claim 1, wherein the target weaning strategy is presented in an interface visually, wherein the target weaning strategy is set based on a clicking or adjusting operation by the user on a point or line presented in the interface.

12. A controller, comprising:

at least one processor; and a memory communicatively connected with the at least one processor;

wherein the memory stores instructions executable by the at least one processor, and the instructions, when executed by the at least one processor, cause the at least one processor to:

receive, before the therapy, multiple weaning strategies inputted into the controller;

store the multiple weaning strategies into the memory;

receive, during the therapy, at least one input of a user, wherein the at least one input corresponds to a clinical decision determined by the user and is used for selecting a target weaning strategy among the multiple weaning strategies stored in the memory, and the at least one input of the user comprises: a time interval of adjusting a flow rate and a FiO2 of a gas provided to the patient; and an adjusting granularity for adjusting the flow rate and the FiO2 of the gas provided to the patient;

set the target weaning strategy selected from the multiple weaning strategies, based on the time interval of adjusting the flow rate and the FiO2 of the gas provided to the patient and the adjusting granularity for adjusting the flow rate and the FiO2 of the gas provided to the patient;

receive a physiological parameter of a patient transmitted by at least one measurement device associated with the patient;

calculate a percentage that a value of the received physiological parameter deviates from a reference value comprised in the set target weaning strategy;

determine that a condition of the patient is stable in a case that the percentage is not greater than a second preset value;

determine that the condition of the patient is not stable in a case that the percentage is greater than the second preset value;

adjust, according to whether the condition of the patient is stable, the flow rate and the FiO2 of the gas provided to the patient, based on the time interval of adjusting the flow rate and the FiO2 of the gas provided to the patient and the adjusting granularity for adjusting the flow rate and the FiO2 of the gas provided to the patient; and output a weaning signal in a case that the flow rate of the gas provided to the patient is less than 10 litre per minute or the FiO2 of the gas provided to the patient is less than 50%, wherein the weaning signal is used to inform the user that the patient can be weaned from the therapy;

wherein the physiological parameter comprises a respiratory rate, and, in a case that the condition of the patient is not stable, the at least one processor is further caused to:

determine whether the respiratory rate is greater than a third preset value, wherein the third preset value is used to determine whether the patient is in a critical state; and output an alarm signal in a case that the respiratory rate is greater than the third preset value.

13. A respiratory device, comprising a controller, wherein the controller comprises:

at least one processor; and a memory communicatively connected with the at least one processor;

wherein the memory stores instructions executable by the at least one processor, and the instructions, when executed by the at least one processor, cause the at least one processor to:

receive, before the therapy, multiple weaning strategies inputted into the controller;

store the multiple weaning strategies into the memory;

receive, during the therapy, at least one input of a user, wherein the at least one input corresponds to a clinical decision determined by the user and is used for selecting a target weaning strategy among the multiple weaning strategies stored in the memory, and the at least one input of the user comprises: a time interval of adjusting a flow rate and a FiO2 of a gas provided to the patient; and an adjusting granularity for adjusting the flow rate and the FiO2 of the gas provided to the patient;

set the target weaning strategy selected from the multiple weaning strategies, based on the time interval of adjusting the flow rate and the FiO2 of the gas provided to the patient and the adjusting granularity for adjusting the flow rate and the FiO2 of the gas provided to the patient;

receive a physiological parameter of a patient transmitted by at least one measurement device associated with the patient;

calculate a percentage that a value of the received physiological parameter deviates from a reference value comprised in the set target weaning strategy;

determine that a condition of the patient is stable in a case that the percentage is not greater than a second preset value;

determine that the condition of the patient is not stable in a case that the percentage is greater than the second preset value;

adjust, according to whether the condition of the patient is stable, the flow rate and the FiO2 of the gas provided to the patient, based on the time interval of adjusting the flow rate and the FiO2 of the gas provided to the patient and the adjusting granularity for adjusting the flow rate and the FiO2 of the gas provided to the patient; and output a weaning signal in a case that the flow rate of the gas provided to the patient is less than 10 litre per minute or the FiO2 of the gas provided to the patient is less than 50%, wherein the weaning signal is used to inform the user that the patient can be weaned from the therapy;

wherein the physiological parameter comprises a respiratory rate, and, in a case that the condition of the patient is not stable, the at least one processor is further caused to:

determine whether the respiratory rate is greater than a third preset value, wherein the third preset value is used to determine whether the patient is in a critical state; and output an alarm signal in a case that the respiratory rate is greater than the third preset value.

14. The respiratory device according to claim 13, further comprising a remote terminal, wherein the controller and the remote terminal are connected communicatively, and the remote terminal is used by the user to import the at least one input for setting the target weaning strategy in a case that the user has an authority for accessing the multiple weaning strategies.

* * * * *